United States Patent [19]

Imachi et al.

[11] Patent Number: 5,413,599
[45] Date of Patent: May 9, 1995

[54] MEDICAL VALVE APPARATUS

[75] Inventors: Kou Imachi, Kamifukuoka; Iwao Fujimasa; Kazuhiko Atsumi, both of Tokyo, all of Japan

[73] Assignee: Nippon Zeon Co., Ltd., Tokyo, Japan

[21] Appl. No.: 165,595

[22] Filed: Dec. 13, 1993

Related U.S. Application Data

[63] Continuation of Ser. No. 342,203, Apr. 24, 1989, abandoned.

[30] Foreign Application Priority Data

Sep. 20, 1988 [JP] Japan ................ 63-233741

[51] Int. Cl.⁶ .............................................. A61F 2/24
[52] U.S. Cl. .......................................... 623/2; 137/854
[58] Field of Search ...................... 604/8, 9; 623/2; 137/854

[56] References Cited

U.S. PATENT DOCUMENTS

| | | | |
|---|---|---|---|
| 2,068,481 | 1/1937 | Brown | 137/854 |
| 2,506,751 | 5/1950 | Trask | 137/854 X |
| 2,742,899 | 4/1956 | Warner et al. | 137/854 |
| 3,228,418 | 1/1966 | Rosback et al. | 137/854 X |
| 3,403,696 | 10/1968 | Pynchon | 137/854 X |
| 3,463,189 | 8/1969 | Fitzpatrick | 137/854 X |
| 4,030,142 | 6/1977 | Wolfe | 623/2 |
| 4,179,757 | 12/1979 | Crawford et al. | 623/2 X |
| 4,222,126 | 9/1980 | Boretos et al. | 623/900 X |
| 4,263,680 | 4/1981 | Reul et al. | 623/2 |
| 4,355,426 | 10/1982 | MacGregor | 623/2 X |
| 4,364,127 | 12/1982 | Pierce et al. | 623/900 X |
| 4,552,553 | 11/1985 | Schulte et al. | 604/9 |
| 4,560,375 | 12/1985 | Schulte et al. | 604/8 X |
| 4,561,129 | 12/1985 | Arpesella | 623/2 |
| 4,574,835 | 3/1986 | Williams | 137/854 X |
| 4,627,836 | 12/1986 | MacGregor | 623/2 X |
| 4,636,194 | 1/1987 | Schulte et al. | 604/9 |
| 4,731,076 | 3/1988 | Noon et al. | 623/2 X |
| 4,823,828 | 4/1989 | McGinnis | 128/205.24 X |
| 4,838,262 | 6/1989 | Katz | 137/854 X |
| 4,861,331 | 8/1989 | East et al. | 604/9 |
| 4,872,867 | 10/1989 | Joh | 604/269 |
| 4,888,009 | 12/1989 | Lederman et al. | 623/900 X |
| 4,934,362 | 6/1990 | Braun | 128/206.15 X |
| 5,002,050 | 3/1991 | McGinnis | 128/205.24 X |

FOREIGN PATENT DOCUMENTS

| | | | |
|---|---|---|---|
| 1106568 | 4/1956 | Germany | 137/854 |
| 1092221 | 7/1958 | Germany | 137/854 |
| 2419926 | 1/1975 | Germany | 623/2 |
| 2750912 | 5/1979 | Germany | 137/854 |
| 0971314 | 11/1982 | U.S.S.R. | 623/2 |

*Primary Examiner*—David H. Willse
*Assistant Examiner*—Bruce E. Snow
*Attorney, Agent, or Firm*—Armstrong, Westerman, Hattori, McLeland & Naughton

[57] ABSTRACT

Disclosed is a medical valve apparatus having a valve assembly which comprises a valve seat and a movable valve, and which is arranged in a duct of a medical appliance, wherein a plurality of through holes for the passage of a fluid are formed through the valve seat, the movable valve is composed of a flexible membrane, and the movable membrane is fixed on the valve seat substantially at the central point thereof. The flexible membrane has a corolla-like shape at the time of a forward flow to allow a free flow of the fluid passing in the through holes, and at the time of a back flow, the flexible membrane is wide-spread to adhere to the valve seat and close the through holes whereby the passage of the regurgitation is prevented. Preferably, the peripheral edge of the valve seat is integrated with the inner wall of the duct of the medical appliance without a seam therebetween.

8 Claims, 4 Drawing Sheets

MEDICAL VALVE APPARATUS

This application is a continuation of application Ser. No. 07/342,203, filed Apr. 24, 1989, now abandoned.

BACKGROUND OF THE INVENTION (1) Field of the Invention

The present invention relates to a medical valve apparatus comprising a valve seat and a movable valve membrane, which is valuable, for example, as an artificial valve apparatus of a pulsatile artificial heart or a pulsatile artificial heart-lung machine.

(2) Description of the Related Art

Recently, development of an artificial heart which exerts the function of the heart auxiliarily and temporarily outside the body at the time of a cardiotomy or other operations, has been developed. This artificial heart consists of a pulsatile blood pump device having a blood inlet port and a blood outlet port, and artificial check valves arranged in the blood inlet port and blood outlet port of this blood pump device to prevent a regurgitation.

A ball valve or a tilting disk valve is known as the artificial heart valve of this type. Namely, an artificial heart valve is known in which a ball or disk-shaped movable occluder is arranged in an opening of a sewn ring usually having a circular shape, and a frame-shaped strut is arranged outside the movable member to prevent dislocation of the movable occluder, wherein the movable member is fitted in the sewn ring upon closure of the valve to prevent a regurgitation, and the movable member moves in parallel or is tilted upon opening of the valve to form a blood passage.

Furthermore, a tricuspidal valve is known resembling a natural valve, which is composed of a natural tissue membrane or a polymer membrane, such as an Ionescu-shiley valve or a Carpentier-Edwards valve.

However, a valve of a clinical valve prosthesis is used as it is for this artificial heart, and accordingly, the cost is high. Particularly, in an artificial valve for an artificial heart, which is used for a relatively short time, and is then discarded the cost is very high. A thrombus is often formed in the gap between the valve ring and the inner wall of the inlet or outlet port of the blood pump device, and the valve is often broken by a water hammer phenomenon which is apt to occur due to pulsation of the fluid.

The tricuspidal valve has a complicated structure, and thus the manufacture is difficult and the cost is high. Furthermore, the tricuspidal valve made of a natural tissue has a problem of calcification in the living body, and in the case of a polymer tricuspidal valve, a thrombus is often formed on the root of the valve cusp.

SUMMARY OF THE INVENTION

A primary object of the present invention is to provide a medical valve apparatus characterized in that the valve has a simple structure and can be made easily, at a reduced cost and from an anti-thrombogenic material, the valve profile is low in the structure, the valve can conform to any optional duct shape, a blood-stagnation does not occur, a thrombus is not formed, and the hemodynamics, especially regurgitation characteristics and the frequency-response characteristics, are improved.

In accordance with the present invention, there is provided medical valve apparatus comprising a valve assembly which comprises a valve seat and a movable valve, and which is arranged in a duct of a medical appliance, wherein a plurality of through holes for the passage of a fluid are formed through the valve seat, the movable valve is composed of a flexible membrane, the movable membrane is fixed on the valve seat substantially at the central point thereof, the flexible membrane has a corolla-like shape at the time of a forward flow to allow a free flow of the fluid passing in the through holes, and at the time of a back flow, the flexible membrane is wide-spread to adhere to the valve seat and close the through holes whereby the passage of the regurgitation is prevented.

DESCRIPTION OF THE PREFERRED EMBODIMENTS

In accordance with a preferred embodiment of the medical valve apparatus of the present invention, the peripheral edge of the valve seat is integrated with the duct of the medical appliance without a seam therebetween.

The construction and function of the medical valve apparatus of the present invention will now be described in detail with reference to embodiments illustrated in the accompanying drawings.

Figure 1A:
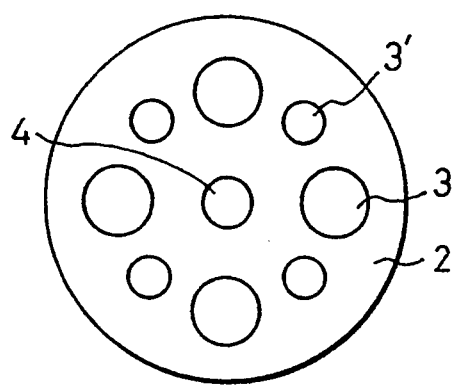
FIG. 1A is a plane view illustrating one embodiment of the valve seat used for the valve apparatus of the present invention.
Figure 1B:
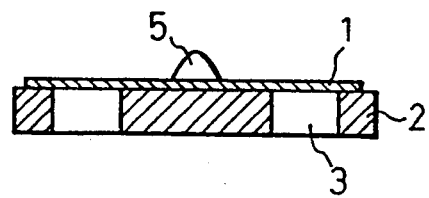
FIG. 1B is a sectional view showing the state where a movable valve membrane is fixed on the valve seat shown in FIG. 1A.

FIG. 1A is a plane view showing an embodiment of the valve seat, and FIG. 1B is a sectional view illustrating the state where the movable membrane is fixed on the valve seat shown in FIG. 1A.

The valve seat 2 shown in FIG. 1A has a disk-like shape, and fluid-passing through holes 3 having a relatively large hole diameter and fluid-passing through holes 3' having a relative small hole diameter are alternately formed and arranged symmetrically on one concentric circle. A screw hole 4 for fixing a setting member for setting a movable valve member is formed at the center of the disk. As shown in Fig. 1B, a movable valve membrane 1 composed of a flexible membrane is mounted on the disk-shaped valve seat 2, and the valve seat 2 and movable valve membrane 1 are fixed at the centers thereof by setting member 5. Also, the setting member 5 can, for example, be screwed into the valve seat 2 for the valve membrane thereto. Further, the central portion of the valve membrane 1 can, for example, be glued onto the central portion of the valve seat 2.

Figure 2A:
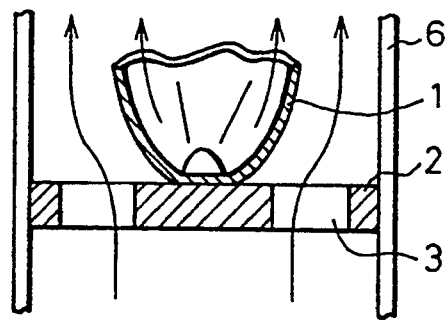
FIGS. 2A and 2B are sectional views showing the state where the valve apparatus of the present invention is used, FIG. 2A showing the state at the time of a forward flow and FIG. 2B showing the state at the time of a back flow.
Figure 2B:
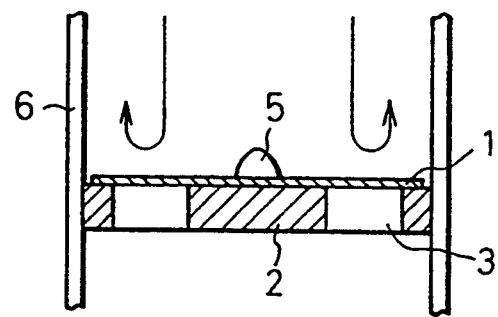

FIGS. 2A and 2B are sectional views showing the state where the medical valve apparatus is used. The disk-shaped valve seat 2 having the movable valve membrane 1 set thereon is fitted in the interior of a duct 6 of a medical appliance. For example, in the case of an artificial heart, the valve seat 2 is attached to the duct 6 of the medical appliance so that the setting side of the movable valve membrane 1 is located on the side opposite to a blood pump (not shown). Blood extruded from the blood pump by the pulsation of the blood pump forms a fair flow in the duct 6 as indicated by an arrow in FIG. 2A and passes through the fluid-passing through holes 3 of the valve seat. The movable valve membrane 1 composed of a flexible membrane has a corolla-like shape at the time of the forward flow to allow a free flow of blood directed to the living body in the case of outlet side. At the time of a back flow, as shown in FIG. 2B, the movable valve membrane 1 is spread flat and adheres to the surface of the valve seat 2 to close the fluid-passing through hole 3 and prevent blood from flowing backward toward the blood pump in the case of outlet side.

The valve seat used for the valve apparatus of the present invention is formed to have a size conforming to the medical appliance to which the valve apparatus is attached, and preferably, as shown in FIGS. 1A and 1B, a plurality of fluid passing through holes 3 and 3' are formed symmetrically on one concentric circle so that turbulent flow does not occur. The diameter and number of the fluid-passing holes are appropriately selected according to the hole shape and the flow quantity and flow rate of the fluid, but in general, preferably the hole diameter is 2 to 5 mm. In the case of circular holes, preferably the hole number is necessary at least 8. If the hole diameter is too large, in the case of a movable membrane composed of a thin film, there is a risk of an intrusion of the membrane into the hole. The shape of the fluid-passing through holes is not limited to a circular shape, and the fluid-passing through holes can have a non-circular cross-section. At least two kinds of fluid-passing through holes differing in shape can be used in combination. Furthermore, the fluid-passing through holes can be long slits (for example, slits shown in FIGS. 3A, 3B and 3C), or a valve seat having a mesh structure as a whole can be used. The shape of the valve seat and movable valve membrane is not limited to a circular shape, and can be fitted to a duct having an optional shape.

Figure 3A:
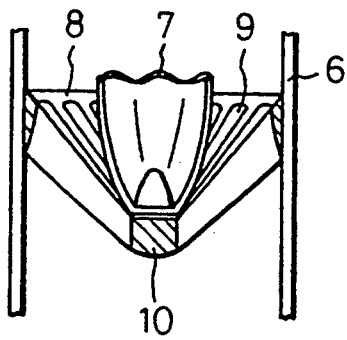
FIGS. 3A, 3B and 3C illustrate another embodiment of the valve apparatus of the present invention, FIGS. 3A and 3B being sectional and plane views showing the state where the valve apparatus is used at the time of a forward flow and FIG. 3C being a sectional view illustrating the state at the time of a back flow or the state where the valve apparatus is not used; and, FIG. 4 is a graph showing the test results of the pump output characteristics in the valve apparatus of the present invention and the Bjork-Shiley valve apparatus.
Figure 3B:
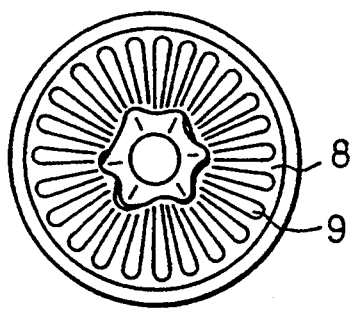
Figure 3C:
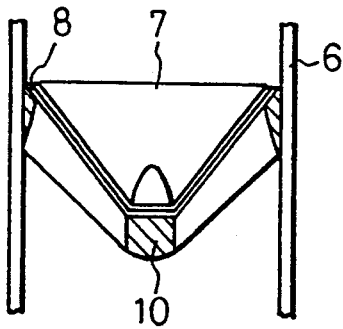

Another embodiment of the medical valve apparatus of the present invention is shown in FIGS. 3A, 3B and 3C. FIGS. 3A and 3B are sectional and plane views illustrating the state where the medical valve apparatus is used at the time of a forward flow, and FIG. 3C is a sectional view illustrating the state of a back flow or the state where the medical valve apparatus is not used. In the valve apparatus of the present embodiment, a funnel-shaped valve seat 8 having many slit-shaped fluid-passing through holes 9 extending in the radial direction and a movable valve membrane 7 having a funnel-like shape conforming to the shape of the valve seat and being composed of a flexible membrane are fixed at the centers thereof by setting member 10. The peripheral edge of the valve seat 8 is integrally attached to the inner wall surface of a duct 6 of a medical appliance. The valve apparatus shown in FIGS. 3A, 3B and 3C has a good response to the flow and subjected to small amounts of flexing, and therefore, this valve apparatus is characterized by a good durability.

A metal such as brass, titanium or stainless steel or a polymer such as polyurethane, polycarbonate, polysulfone, nylon, polyacetal or epoxy is preferred as the material of the valve seat.

The movable valve membrane arranged on one surface of the valve seat is preferably an elastomer film having a good durability, which is composed of an anti-thrombogenic material. Preferably, the thickness of the film is 0.1 to 0.4 mm, and segmented polyurethane or a polyurethane/polysiloxane copolymer are especially preferred as the film material.

The movable valve membrane is fixed substantially at the center thereof to the valve seat. The fitting means is not particularly critical; for example, screwing or bonding with an adhesive can be adopted.

The assembly comprising the movable valve membrane and valve seat is attached to a predetermined position in a blood inlet or outlet port of a medical appliance, for example, a blood pump for an artificial heart. The attachment means is not particularly critical, but the valve member should be attached so that a fluid-stagnation does not substantially occur. If the valve seat is integrally formed with the duct of the medical appliance and then the movable valve membrane is fixed to the valve seat, since the valve seat is integrated with the duct without a seam formed therebetween, the anti-thrombogenicity is further improved. To further improve the anti-thrombogenicity, a known anti-thrombogenic material can be used for each of the valve seat, the movable valve membrane, and the duct.

As apparent from the above description, the medical valve apparatus of the present invention has a relatively simple structure, is easily manufactured, and has a low manufacturing cost.

The valve apparatus is constructed so that a stagnant portion is not formed, and a thrombus is rarely formed. Especially, the movable valve membrane exerts a function of washing the central portion of the valve membrane-valve seat fixed point by the flapping. Accordingly, the defect of a conventional valve in which an annular flow is formed, such as a ball valve or a disk valve, that is, the stagnation of the fluid in the central portion, can be overcome. In the valve apparatus where the peripheral edge of the valve seat is integrally formed with the inner wall of the duct without a seam by integral molding, the anti-thrombogenicity can be further improved.

As shown in the example given hereinafter, the hydrodynamic characteristic of the medical valve apparatus of the present invention is substantially the same as that of the conventional Bjork-Shiley valve and has a frequency-response characteristic superior to that of this conventional valve.

The shape of the medical valve apparatus of the present invention is not limited to the conventional circular shape, and a valve apparatus having an optional shape, such as an ellipsoidal shape or a square shape, can be easily prepared. This is another advantage of the present invention.

EXAMPLE

A valve seat-valve membrane assembly shown in FIG. 1B was fabricated by using a valve seat and a movable valve membrane. The assembly was arranged in a duct of a medical appliance described below to construct a valve apparatus. The hydrodynamics, the frequency-response characteristic and the state of the flow around the valve were observed. Valve seat:

A valve seat made of brass and having a diameter of 16 mm, in which four through holes having a diameter of 3 and four through holes having a diameter of 4 mm were formed symmetrically on one concentric circle.

Movable valve:

A movable valve membrane made of a polyurethane/polysiloxane copolymer and having a thickness of 0.2 mm. Medical appliance:

A sac-type blood pump for an artificial heart.

The valve seat-movable valve membrane assembly was charged in each of the inlet and outlet ports of the pump, and the test was carried out under conditions such that the blood introduction pressure was 4.5 cmH$_2$O, the blood discharge pressure was 100 mmHg, the pumping rate was 100 bpm, and the driving positive and negative pressures were 200 mmHg and −40 mmHg, respectively.

For comparison, the same test was carried out by using a Bjork-Shiley valve assembly described below.

Bjork-Shiley valve assembly:

A valve seat made of a Stellite alloy and having a diameter of 16 mm, and a movable valve body composed of pyrolitic carbon and having a diameter of 15.9 mm.

Figure 4:
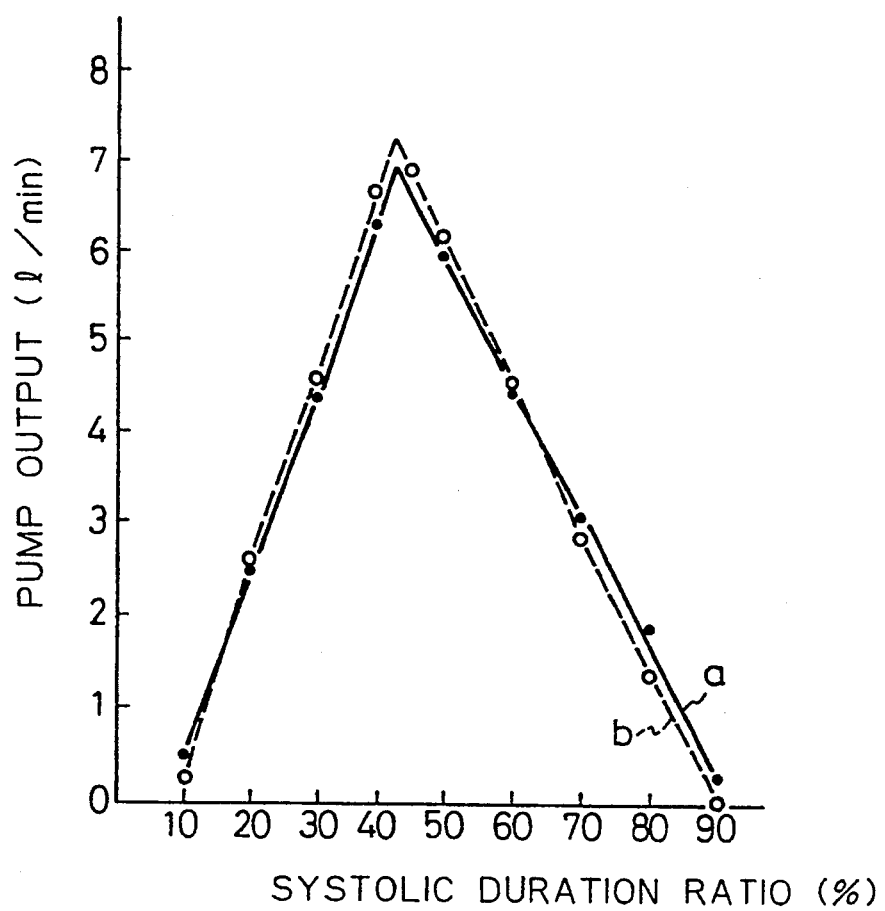

The results of the test of the hydrodynamic characteristic of the pump are shown in FIG. 4. In FIG. 4, the solid line (a) indicates the characteristic of the valve apparatus of the present invention and the dotted line (b) indicates the characteristic of the Bjork-Shiley valve apparatus. It is seen that the hydrodynamic characteristic of the valve apparatus of the present invention is substantially the same as that of the Bjork-Shiley valve apparatus.

In the valve apparatus of the present invention, the quantity of regurgitation at the closing of the valve was smaller than in the Bjork-Shiley valve apparatus, and the quantity of the regurgitation was zero after the closure of the valve. Furthermore, the valve of the present invention faithfully followed a pulsation frequency of 300 pulses per minute and the frequency response characteristic was very good. At the visualization test of the flow, it was found that the central portion was thoroughly washed at the opening of the valve, and stagnation of the flow did not occur.

We claim:

1. A medical valve placed in a tubular duct of at least one of an artificial heart device and an artificial heart-lung device capable of passing a first flow of a liquid but interrupting a second flow which flows in an opposite direction to the first flow, the medical valve comprising:

a substantially circular valve seat, having a substantially flat surface, provided in the tubular duct, having the valve-seat surface at one side of said valve seat, said valve-seat surface being located at a downstream side of the first flow, said valve seat further having a plurality of small through holes substantially evenly allocated thereupon except for a central part thereof; and a flexible flap provided solely at the downstream side of the valve seat and having a surface area slightly smaller than that of the circular valve seat in a manner such that the flexible flap covers all the plurality of small through holes, the flexible flap being fixed to the central part of the valve-seat surface, wherein a circumferential part of the flexible flap moves apart from the valve-seat surface so as to pass the first flow while the circumferential part sealingly adheres to the valve-seat surface so as to interrupt the second flow, wherein the flexible flap is made of a copolymer film which is comprised of polyurethane and polysiloxane and has a thickness of 0.1 to 0.4 mm said copolymer film having at least anti-thrombogenic properties for the passage of blood.

2. A medical valve as set forth in claim 1, wherein the valve seat and the duct are intergrally formed of a similar material.

3. A medical valve as set forth in claim 1, wherein a shape of each of the valve seat surface and the flexible flap is flat.

4. A medical valve as set forth in claim 3, wherein the flexible flap is substantially circular.

5. A medical valve as set forth in claim 1, wherein the shape of each of the valve seat surface and the flexible flap is substantially conical.

6. A medical valve as set forth in claim 1, wherein the plurality of small through holes are provided symmetrically around the central part.

7. A medical valve as set forth in claims 1, wherein substantially one-half of the small holes are smaller than substantially another half of the small holes.

8. A medical valve as set forth in claim 1, wherein each small through hole is an elongated slit extending radially from the central part.

* * * * *